United States Patent
Lavery et al.

[11] Patent Number: 6,090,548
[45] Date of Patent: *Jul. 18, 2000

[54] METHOD FOR IDENTIFYING AND/OR QUANTIFYING EXPRESSION OF NUCLEIC ACID MOLECULES IN A SAMPLE

[75] Inventors: Daniel Lavery, Bernex; Ueli Schibler, Borex, both of Switzerland

[73] Assignee: Roche Diagnostics GmbH, Penzberg, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/855,321

[22] Filed: May 13, 1997

Related U.S. Application Data

[60] Provisional application No. 60/018,355, May 14, 1996.

[51] Int. Cl.$^7$ .............. C12Q 1/68; C12P 19/34; C07H 21/02; C07H 21/04
[52] U.S. Cl. ............ 435/6; 435/91.1; 435/91.2; 536/24.3; 536/23.1; 536/24.31; 536/24.32; 536/24.33
[58] Field of Search .............. 435/6, 91.1, 91.2; 536/24.3, 24.31, 24.32, 24.33, 23.1

[56] References Cited

U.S. PATENT DOCUMENTS

| | | | |
|---|---|---|---|
| 5,436,142 | 7/1995 | Wigler et al. | 435/91.2 |
| 5,501,964 | 3/1996 | Wigler et al. | 435/91.2 |
| 5,726,022 | 3/1998 | Burmer et al. | 435/6 |

FOREIGN PATENT DOCUMENTS

| | | |
|---|---|---|
| WO8912695 | 12/1989 | WIPO . |
| WO 96/40998 | 12/1996 | WIPO . |

OTHER PUBLICATIONS

Perkin Elmer Biotechnology Catalog, p. 26, 1992.
Dynal, Biomagnetic Techniques in Molecular Biology, Technical Handbook, Second Edition, pp. 120–127, 139 and 153–157, 1995.

*Primary Examiner*—Jeffrey Fredman
*Attorney, Agent, or Firm*—Fulbright & Jaworski, LLP

[57] ABSTRACT

The invention involves methods for quantifying or identifying nucleic acid molecules in samples. The method involves using different, double stranded additions to nucleic acid molecules, followed by cross hybridization and identification of one type of molecule.

8 Claims, 4 Drawing Sheets

METHOD FOR IDENTIFYING AND/OR QUANTIFYING EXPRESSION OF NUCLEIC ACID MOLECULES IN A SAMPLE

This application claims benefit of U.S. Ser. No. 60/018,355 filed May 14, 1996.

FIELD OF THE INVENTION

This invention relates to methods for identifying and/or quantifying expression of nucleic acid molecules in a sample. Specifically, it relates to the use of modified amplification systems, such as a modified polymerase chain reaction ("PCR").

BACKGROUND AND PRIOR ART

In many biological systems, changes in expression of certain genes can, and do, lead to dramatic changes. Phenotypically, these changes may include developmental fate determination, cell death, and oncogenesis. Hence, identification of these genes is clearly of great interest; however, such identification is often difficult, because the level of expression may be very low, or changes in expression may be very subtle. For example, certain mRNA molecules representative of transcription factors may be present as a single copy per 10,000 mRNA molecules.

The issues and interest touched upon supra have led to development of many methodologies. While these methods all have certain benefits, they also exhibit drawbacks which limit their efficacy and applicability. One major drawback of all of the methods is that they do not offer convenient procedures for identification of low abundance molecules, which differ by 10-fold or less relative to controls.

The first class of prior art methodologies are the "non-selective" systems. Differential screening is one such approach. It involves screening a library, in duplicate, using labelled cDNA from two different RNA populations. Relative signal intensity of plaques or colonies after probe hybridization, theoretically, represents the abundance of cDNA in the probe population, and, hence, differences in signal should represent clones which are differentially expressed.

The problem with this system is that it is functional only with high abundance RNA. Low abundance species are underrepresented in both library and probe populations. As a result, there are problems with screening large numbers of plaques or colonies and one is forced to use probes of extremely high specific activity, with long incubation times, in order to secure a significant signal.

A second method of this type is the differential display system, described by, e.g., Liang, et al., Science 257:967 (1992). In this system, random PCR products are generated for display on polyacrylamide gels. A simple visual comparison of patterns between gels should permit identification of species which differ in abundance. The problem with differential display is that it is extremely labor-intensive, due to the number of primer pairs and sequencing gel runs needed to cover statistically significant portions of the population. Further, no selection is used against relatively abundant, non-differentially expressed species, and these species may obscure the detection of less abundant species of interest.

In contrast to the methods discussed supra, so-called selective methods afford some ability to separate out molecules of interest. In subtractive hybridization, single stranded cDNA or RNA from a population of interest (the "tester" population), is hybridized with an excess, generally 100- to 1,000-fold, of complementary, single-stranded cDNA or RNA from a control population (the "driver" population). Double-stranded hybrids, which represent species shared between driver and tester, are "subtracted" from the mixed population. Generally, this is accomplished by hydroxyapatite columns chromatography or by tagging cDNA with biotin, followed by removal of biotin containing complexes with streptavidin. Any remaining, unhybridized molecules are then used for subsequent analyses. See Milner, et al., Nucleic Acid Res. 23:176 (1995), for a review of this technology.

This methodology, however, is of limited application. First, species in the tester population whose difference in abundance from the driver population is less than the excess of driver-to-tester in mixed population, will be lost prior to subtractions. Second, "subtraction" of hybrid molecules by column chromatography/biotin extraction is a "negative" purification, relying on removal of unwanted molecules, rather than the desired forms. Any unwanted molecules which are not removed will interfere with subsequent experimentation. Further, as the kinetics of hybridization approach but do not reach completion, any unwanted molecules which have not hybridized will contaminate the tester population. When the desired species are low in abundance, even low absolute amounts of contamination may obscure detection.

Competitive hybridization, in contrast to subtractive hybridization, uses competition between two, denatured populations of cDNA. Either hetero-hybrids of driver/tester strands, or homo-hybrids result. To carry out these assays, two double-stranded populations are mixed, denatured complexity, and allowed to re-associate. Random assortment presumes re-association with a probability based upon relative abundance. Hence, if a cDNA species is present, at a higher concentration in the tester population than the driver population, tester homo-hybrids make up a greater proportion of the hybrids than homo-hybrids of a cDNA species present in equal quantities in both populations.

Any tester homo-hybrids are removed, and represent the selected population. This differential enrichment is the basis for subsequent enrichment by competitive hybridization.

The main problem with this methodology is that it relies on efficient recovery of tester homo-hybrids for effective enrichment. If the driver:tester ratio is high, the fraction of molecules found as tester homo-hybrids is very low, and purification steps must be very precise, and/or repeated frequently.

Competitive hybridization methods have found wide use. One method, disclosed by Wang, et al., Proc. Natl. Acad. Sci. USA 88:11505 (1991), utilized biotinylated driver cDNA, with separation by streptavidin binding and organic extraction. Zeng, et al. Nucleic Acids Res. 22:7381 (1994) disclose a method where tester molecules are tagged with thiolated nucleotides. As homo-hybrids, these molecules resist digestion by exonucleases III and VII. Yet a further method, that of Klickstein, in Ausubel, et al., ed. Current Protocols In Molecular Biology (Wiley & Sons, N.Y., 1995), pages 5.8.9 to 5.8.15, uses compatible restriction site overhang sequences which are present only on tester molecules, thereby permitting cloning of only tester homo-hybrids. Lisitsyn, et al., Science 259:946 (1993), teach a method where PCR primers are ligated to tester molecules, such that only tester homo-hybrids are exponentially amplified.

The method of Wang and Zeng are not satisfactory, because both are negative enrichments. Even reaction efficiencies of greater than 99% may not be sufficient to prevent contamination by unwanted species. Klickstein and Lisitsyn are positive selection methods but are labor-intensive.

Competitive hybridization suffers from two additional problems. The first, the so-called "Cot problem", stems from the fact that only double-stranded tester homo-hybrids are selected after hybridization. As a result, if hybridization does not proceed beyond a $Cot_{1/2}$ value sufficient for low abundance species, the fraction, or a large portion of it, is lost during selection. Further, there is the problem of "preferential amplification", discussed infra.

Hence, there is clearly a need for an improved method for identifying and/or quantifying nucleic acid molecules in a sample, especially those mRNA molecules which are present in low abundance (about 100 molecules or less per cell). The particulars of the inventive methods, which address these problems, are set forth below.

DETAILED DESCRIPTION OF PREFERRED EMBODIMENTS

Figure 1:
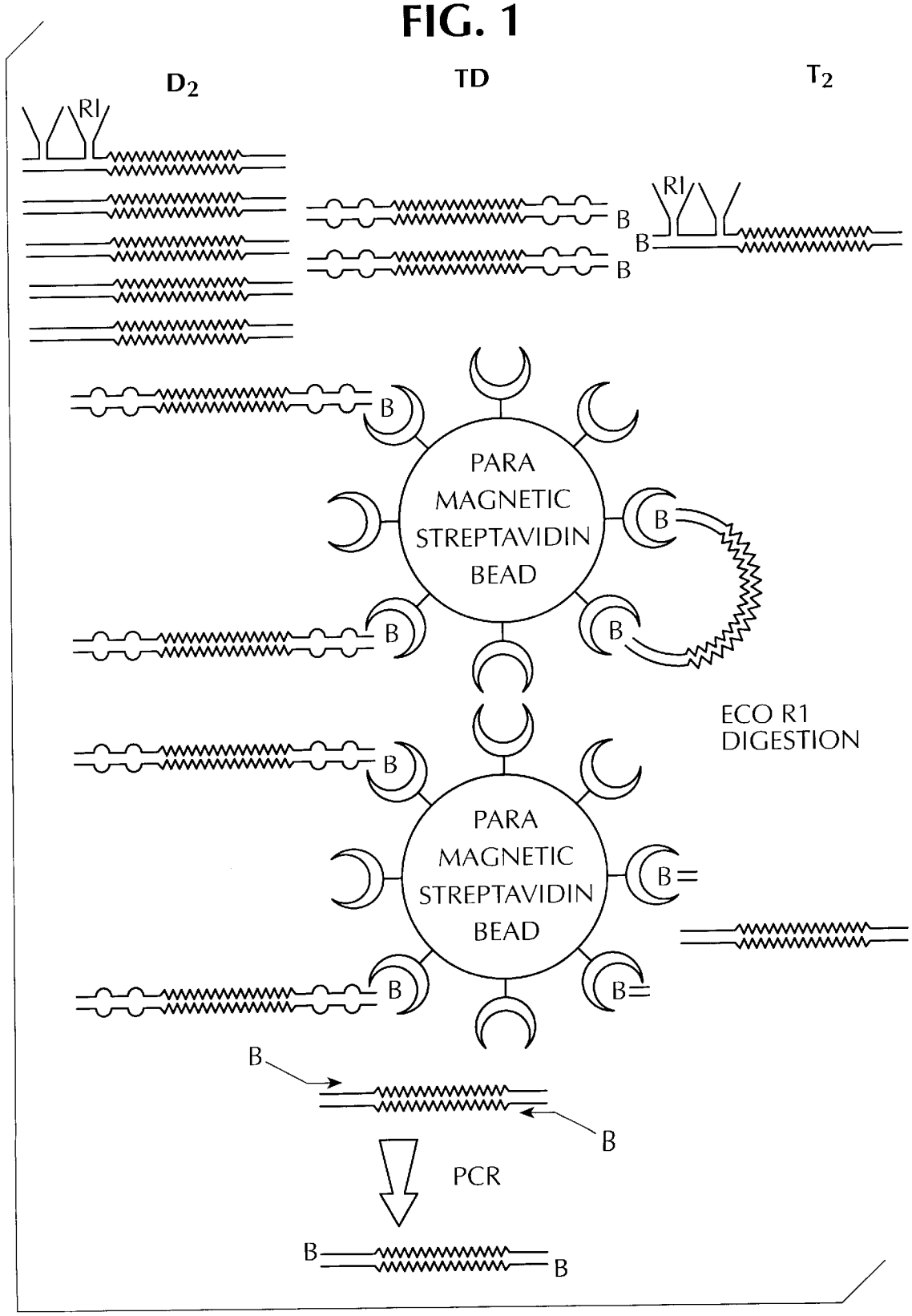
FIG. 1 shows, pictorially, an embodiment of the invention.

The invention involves the use of detectable binding partners, as well as the introduction of cleavable, or removable sequences in a target population. More specifically, a target population is treated, using art-recognized techniques, to add relatively short double-stranded nucleotide sequences to its ends. These sequences are chosen so that one strand is a recognition and cleavage site for an endo-nuclease and the others is its complement.

Following treatment of the sample as indicated, a primer is added. The primer may comprise a nucleotide sequence which constitutes a recognition and cleavage site for an endo-nuclease or the complement of such a sequence with a first member of a binding pair attached to the sequence at its 5' end.

The primers are then amplified, using art-recognized techniques, to create an amplified population which can be depicted as:
(Binding Partner)—5' Cleavage Site (N)n—cleavage site 3'
  3' Cleavage Site (N)n—cleavage site 5'—(Binding Partner)

The driver population is also treated to have a short double-stranded nucleotide sequence added at its end. This sequence is specifically chosen not to be a restriction endo-nuclease cleavage site. Primer is added, but the primers user in the driver sample are specifically not-labelled. Amplification follows, and the tester and driver samples are mixed.

Any tester:tester hybrids which form will have binding partner and cleavage sites in the homohybrid. Such complexes can be removed by contact of a solid phase with a second binding partner which binds to the first one (e.g., (strept)avidin-biotin-antigen-antibody, acten-carbohydrate), etc. so, too, will heterohybrids, which contain one molecule of the tester population. Any homohybrids from the driver population will not be removed.

The immobilized sample is now purified further. Heterohybrids, while containing binding partner, will not contain a restriction endonuclease recognition and cleavage site, because molecules from the driver population were not treated to present these. Thus, one removes the desired, tester molecules by cleaving them with an endo-nuclease, e.g.. The process can then be repeated as many times as is desired or necessary.

Particulars of the method are set forth in the following examples.

EXAMPLE 1

This example describes the cloning of a cDNA restriction fragment length polymorphism, or "RFLP", linked to a selected allele.

"DBP" is a transcription factor found at elevated levels in liver cells. Using gene replacement techniques, a mouse strain which was homozygous for a disrupted allele of this gene was developed, using well known techniques. The goal of this disruption was to determine if disruption of DBP would alter expression of other genes.

As a start, poly(A) mRNA was isolated from the liver cells of the above references "knock-out" mice, and from liver cells of control mice. These control mice were non-isogeneic mice derived from the same cross (C57/Black 6×OLA 29) used to generate the knock-out mice. A cDNA library was generated from both sets of mRNA, which was then digested with restriction endo-nuclease Sau3AI (/GATC). Other restriction endonucleases which recognize sequences of four nucleotide bases, and cleave therein, such as RsaI (GTAC) can be used.

It was not known if the DBP alteration would lead to an increase or decrease in gene expression—assuming it had any effect at all. Thus, two sets of experiments were carried out. In one, the knock-out mouse library was the tester population with the control library serving as driver, with roles being reversed for the second set of experiments. Each set of experiments used driver/driver hybridization to control preferential amplification.

Following preparation of the libraries, PCR was again used to tag populations differentially. The tester primer had, as 5' sequence, CACACA and located close to the 5' end, the EcoRI recognition and cleavage site GAATTC. Alternatively, a BamHI recognition and cleavage site (G/GATCC) is used, when Sau3AI was used to digest the cDNA library, or an Asp718I recognition and cleavage site (G/GTACC) when the library was digested by RsaI.

The driver primer was not biotinylated and was identical in sequence primer to the tester at its except that the EcoRI recognition and cleavage site was eliminated by changing the sequence to GATATC.

Amplifications was carried out using either Taq polymerase, or a mixture of DNA polymerases, via PCR, following well known techniques. Yields were quantitated by trace labelling of the reaction with $[\alpha-^{32}P]$ dATP, with free nucleotides being removed via isopropanol precipitation, or by calculating PCR products on agarose gels. When determinable groups are incorporated, via PCR, one can use a photometer in calculating PCR products on the agarose gel.

Populations were then mixed. The first round of hybridization was at a driver:tester ratio of 20:1 to 50:1. Subsequent rounds were carried out at 20 to 50:1 ratios.

In the experiments, double-stranded cDNA was denatured by heating at 75° C. in formamide without salt, for a total of 5 minutes. Quick cooling on ice followed, then the samples were collected via a brief centrifugation period.

The collected, denatured cDNA was combined with 1M NaCl, 10 mM Tris (pH 8.5), 1 mM EDTA, and 50% formamide to a final concentration of 5 mg/ml. This hybridization mix was transferred to glass capillaries sealed, and allowed to hybridize at 40° C. for 72 hours.

Following the hybridization reaction, the mix was harvested, in 200 μls of 2× mung bean nuclease buffer. Free primers and unhybridized, single-stranded species were eliminated by digestion of one half of the hybridization mix with 0.3 units of mung bean nuclease buffer per ug of DNA, in a final reaction of 200 μls of 1× mung bean nuclease buffer, for 30 minutes at 30° C.

The reaction was stopped with SDS and EDTA, extracted with phenol/chloroform, and then precipitated with EtOH.

In an alternate procedure, double stranded cDNA was dissolved in 6 μl of PERT buffer (15M NaSCN, 120 mM Tris/HCl, pH 8.5, 10 mM EDTA, 8% phenol). The solution was denatured by heating to 98° C. for 10 minutes. Following hybridization, as discussed supra, 200 μl of mung bean nuclease buffer, and 4 U of mung bean nuclease were added, and incubated for 30 minutes, at 30° C.

Using either of the methodologies set forth, supra, approximately one half of the nuclease-treated sample was then bound, in the presence of 1 mM heparinsulfate to paramagnetic beads which had been pretreated with 1 mM heparinsulfate to which streptavidin had been conjugated. The bead and sample were mixed in 0.4 μl of binding buffer, using sufficient beads to ensure that the binding capacity was not exceeded by the sample.

Following two hours of gentle rotation, which facilitates the streptavidin biotin binding, the beads were washed, twice, for 10 minutes at 60° C. in a buffer (50 mM NaCl, 10 mM Tris/HCl, pH 8.5, 0.1 mM EDTA, 0.1% Triton), and re-suspended in 30 μls of EcoRI restriction digestion buffer. An endonuclease (EcoRI, BamHI, or Asp 718I) was added, at 32 U per mg of tester in the reaction (volume: 30 μls), and digestion was facilitated by incubation at 37° C. for 60 minutes, with gentle mixing every 5 minutes to maintain the suspension. Following this digestion/incubation period, volume was increased to 200 μls, the beads were removed using magnetic separation (repeated twice). The selected supernatant was then extracted with phenol chloroform, chloroform, and ether (two separations for each).

For repeated rounds of selection, 10 μls of selection product were used for PCR amplification. The protocols were the same as above, except the sequences which are 5' to the tester primer EcoRI, BamHI, or Asp 718I) cleavage site were different. This change is to prevent favored amplification of any contaminating molecules which were carried through selection.

The primers were alternated as the selection rounds were repeated.

Figure 2A:
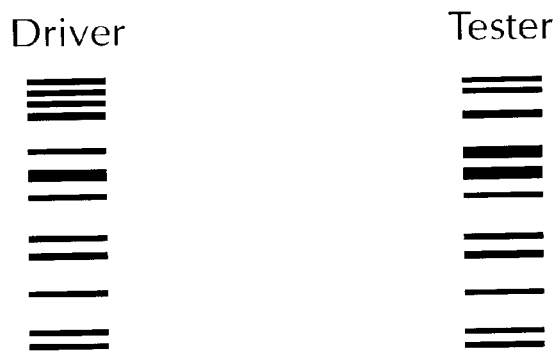
FIG. 2a compares an auto-radiograph of driver and tester populations before amplification.
Figure 2B:
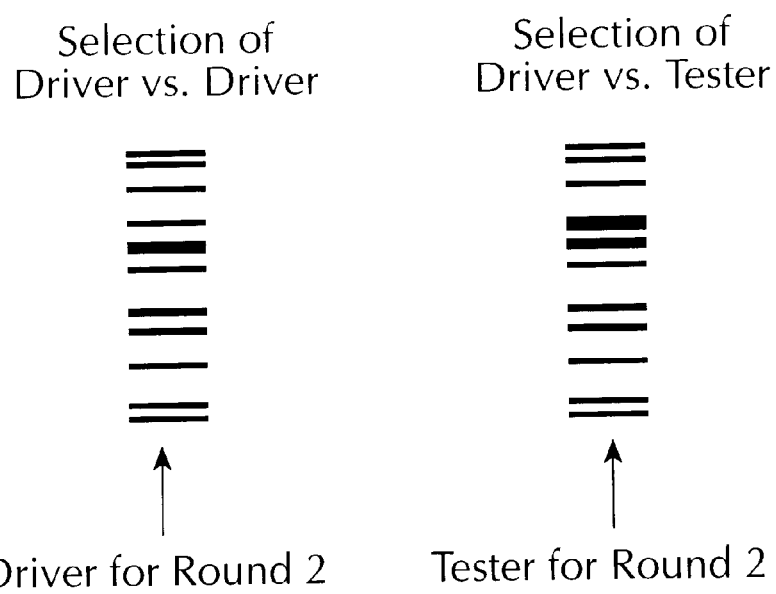
FIG. 2b compares the same samples after four rounds of amplification and selection.

FIGS. 2a and 2b show some of the results. In FIG. 2a, polyacrylamide gel resolution of radiolabelled species are presented, prior to the amplification protocols. One species does appear amplified relative to the others. Following one round of amplification, (FIG. 2b), the difference is much more pronounced.

Following three rounds of amplification, one particular species was sufficiently enriched so that it could be isolated from the gel, cloned, and sequenced. Analysis showed the sequence to be a polymorphic allele of a ferritin light chain gene, although these data are not presented. The polymorphism resulted in creation of an additional Sau3AI site in the allele, which is not present in other alleles in the mouse population sampled. The ferritin light chain gene is known to be closely linked to the DBP gene in humans; therefore, selection of the mutant DBP gene during generation of the knock-out strain probably selected for the Sau3AI polymorphic allele of the ferritin light chain gene, due to linkage in the DBP knock-out allele. Every animal in the knock-out pool would carry the RFLP.

In contrast, the allele is not selected for within the non-isogenic control, resulting in expression in only a fraction of the control pool. Thus, the method was able to amplify the differential.

EXAMPLE 2

The power of the technique described herein was shown in a set of experiments designed to detect mRNAs expressed at higher levels in the evening that the morning patterns.

Using the same protocols set forth in example 1, an Sau3AI cDNA library was prepared using mRNA isolated from mouse liver at 8:00 AM, and a sample taken from the same cells at 8:00 PM. The 8:00 AM library was used as driver population, and the 8:00 PM library as tester population. The starting tester (8:00 PM), and driver (8:00 AM) populations are shown in FIG. 2a, which shows that the vast majority of species concentrations are similar in the two populations.

After two rounds of selection, a species appeared to be enriched in the selected population but nor in the control. By the fourth round, the species represented the major species in the entire population. This is depicted in FIG. 2b. The asterisked denotes the species which differed in the samples.

Following sequence analysis, this species was identified as an Sau3AI fragment of cDNA which corresponds to murine testosterone 15α-hydroxylase ("TH").

EXAMPLE 3

Following the results of example 2, the expression of TH mRNA in the liver during the day was quantitated.

Figure 3:
FIG. 3 presents data showing that species identified using the inventive method display circadian accumulation, i.e., the species which are present at different concentrations at different times of day can be identified.
Figure 4:
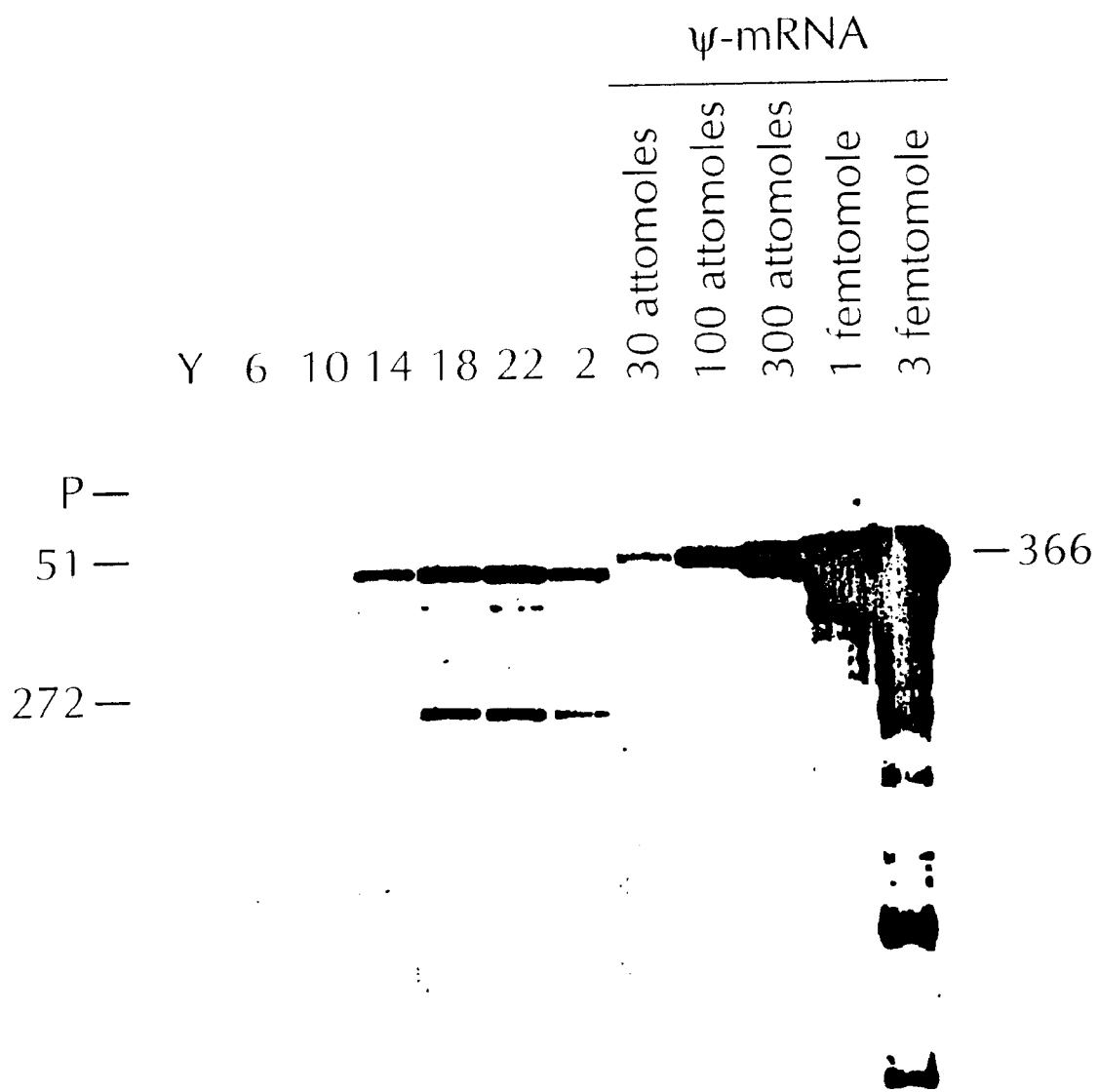
FIG. 4 shows results obtained following quantitation of mRNA.

Total RNA was extracted from murine liver cells at various points in time over a day. The time intervals are indicated in FIG. 3, discussed infra.

Ten μg of total RNA were used, taken from two samples, at different points in time. These samples were used in RN-ase protection assays using, as a probe $\alpha$-$^{32}$P labelled anti-sense T3 RNA transcript of the 15α hydrolase cDNA Sau3AI fragment, as discussed supra. This probe generates a 351 base-protected RNA fragment for Type II TH cDNA, and a 272 base-protected RNA fragment for Type I TH cDNA. Parallel to this, RN-ase protection assays were performed using a non-radiolabelled, sense strand pseudo mRNA (Ψ-mRNA), which corresponded to the TH cDNA Sau3AI fragment, together with the probe used for the other samples. The Ψ-mRNA protected a fragment of 366 bases, when hybridized to the Sau3AI probe. When a known molar quantity (from 3 fmoles to 30 amoles in these experiments) of Ψ-mRNA was added to the reaction, the resulting signal was used to generate a standard curve to estimate molar quantity of mRNA in the total RNA sample.

It is known that 10 ug of total RNA represents about $2 \times 10^5$ liver cells (see, e.g., Schmidt, et al., J. Cell Biol. 128: 467 (1995). The accumulation of TH mRNA was estimated to be approximately 50 to 60 copies per cell at 10:00 AM, and 300 copies per cell at 10:00 PM ("10" and "22" in the figure, respectively). Thus, the methodology permitted precise quantitation of species representing very low abundance mRNAs with modest (5 to 6-fold) concentration differences between tester and driver populations.

In addition to the usefulness of the invention described herein for determining species at low copy number, the invention is useful in addressing what is perhaps the most time- and labor-intensive stage of subtractive cloning, i.e., the identification and characterization of the enriched products of the selection. In this stage, the true positive species are distinguished from the false positive species which arise as artifacts solely due to the selection process itself. In selection methods based on PCR-amplified samples, the generation of false positives is largely due to the fact that PCR amplification is not equally efficient for every species in a complex sample population. This can dramatically alter the make-up of any complex sample undergoing PCR amplification. In the case of the invention, a method such as PCR is used to amplify the small amount of selected sample at the end of the procedure. In addition, one great advantage of the invention over other selection methods is its ease in supporting multiple rounds of selection, thus requiring multiple rounds of amplification. Therefore, when comparing two samples in order to detect very slight differences in their make-up, random PCR-induced changes in the tester population can overtake the enrichment of species resulting from true selection. This is especially evident in FIG. 2b, which demonstrates that the overall size distribution in samples selected four times is significantly larger than the overall size distribution in the starting populations (FIG. 2a).

The basis of PCR artifact correction is the following: for each hybridization of tester and driver, the driver sample used is one which has undergone the same number of selection and amplification steps as the tester, rather than the "original driver" sample. This is because the "original driver" sample has not undergone multiple rounds of selection and PCR, and thus does not contain increases in the concentration of certain species which were introduced in the tester sample by the experimental manipulations themselves. To correct for these artificial changes in the tester sample, a parallel hybridization is always carried out, in addition to the hybridization of biotinylated, EcoRI site-containing tester DNA and non-biotinylated, EcoRI site-mutated driver DNA. In this parallel hybridization, the driver DNA is hybridized to itself, using DNA amplified from the driver sample using the biotinylated, EcoRI site-containing primer (usually the "tester primer"), mixed with DNA amplified from the driver sample as before, with the non-biotinylated, EcoRI site-mutated "driver primer". In this control "autohybridization", the "tester" and "driver" are both derived from the same driver nucleic acids. There, as these samples are theoretically identical, selection of "tester" homohybrids from this hybridization by binding to biotin and cleaving with EcoRI should yield a sample which is identical to the starting driver population. However, if there are changes in the make-up of the selected sample due to the experimental manipulations (PCR amplification, etc.), these will be represented in the selected "autohybridization" sample. These artificial changes should also have occurred in the tester sample resulting from the tester-driver hybridization selection. Therefore, if one takes the "selected driver" rather than the "original driver" as the driver for the next round of hybridization with the "selected tester", the artificial changes found in the "selected tester" sample will also be found in the "selected driver" hybridization partner, and thus will be corrected during the selection procedure.

It is believed that the method described herein is the first system to provide such PCR artifact correction. Other systems such as EDS (zeng et al., Nucl. Acids Res. 22: 4381) do not account for PCR artifact correction, so many false positive species were generated.

What is claimed is:

1. Method for removing a desired nucleic acid molecule form a sample, comprising:
   (i) contacting said sample with a double-stranded nucleic acid molecule which comprises a restriction endonuclease recognition and cleavage site,
   (ii) attaching said double-stranded nucleic acid molecule to nucleic acid molecules in said sample,
   (iii) contacting said sample with a primer molecule which consists of: (a) a single-stranded nucleic acid molecule complementary to on strand of said double-stranded nucleic acid molecule, and (b) a first member of a binding pair attached to the 5'-end of said single-stranded nucleic acid molecules,
   (iv) amplifying said sample with said primer,
   (v) admixing said sample with a second sample of nucleic acid molecules, wherein at least a portion of nucleic acid molecules in said second sample are capable of hybridizing to nucleic acid molecules in said first sample, wherein the nucleic acid molecules in said second sample have (a) a double-stranded nucleic acid molecule attached thereto which differs from the double-stranded nucleic acid molecule attached in (iii), said double-stranded nucleic acid molecule not being cleavable by the restriction endonuclease which cleaves the double-stranded nucleic acid molecule of (i),
   (vi) treating admixed samples to cause hybridization there between,
   (vii) contacting said admixed samples with a second member of a binding pair which binds to said first member of a binding pair,
   (viii) removing any molecules which contain bound said first and second member of a binding pair,
   (ix) contacting molecules removed in (viii) with a restriction endonuclease which recognizes and cleaves any nucleic acid molecule which comprise the double-stranded nucleic molecule of (ii) but not any double-stranded nucleic acid molecules formed by hybridization of a single-strand nucleic acid molecule of said first sample and a single strand nucleic acid molecule of said second sample or double-stranded nucleic acid molecules of said second sample,
   (x) separating any cleaved molecules therefrom.

2. The method of claim 1, wherein said first member of a binding pair is biotin.

3. The method of claim 2, where said second member of said binding pair is avidin or streptavidin.

4. The method of claim 1, wherein said second member of a binding pair is bound to a solid phase.

5. The method of claim 4, wherein said solid phase is a magnetic particle.

6. Method for identifying a nucleic acid molecule of interest, comprising amplifying any nucleic acid molecules removed in claim 1.

7. The method of claim 1 wherein the double stranded nucleic acid molecule attached to said nucleic acid molecules in the second sample has a restriction endonuclease site which differs from the restriction endonuclease site of the double stranded nucleic acid molecule of (ii).

8. The method of claim 1, further comprising repeating said steps (i) through (x) with separated cleaved molecules.

* * * * *